US006645525B1

(12) United States Patent
Woiszwillo

(10) Patent No.: US 6,645,525 B1
(45) Date of Patent: Nov. 11, 2003

(54) IONICALLY FORMULATED BIOMOLECULE MICROCARRIERS

(75) Inventor: James E. Woiszwillo, Milford, MA (US)

(73) Assignee: Sedum Laboratories, Inc., Mansfield, MA (US)

( * ) Notice: Subject to any disclaimer, the term of this patent is extended or adjusted under 35 U.S.C. 154(b) by 0 days.

(21) Appl. No.: 10/018,991

(22) PCT Filed: Jun. 23, 2000

(86) PCT No.: PCT/US00/17223

§ 371 (c)(1),
(2), (4) Date: May 6, 2002

(87) PCT Pub. No.: WO01/01964

PCT Pub. Date: Jan. 11, 2001

Related U.S. Application Data

(60) Provisional application No. 60/140,623, filed on Jun. 23, 1999.

(51) Int. Cl.$^7$ .......................... A61K 9/64; A01N 37/18; B32B 15/02
(52) U.S. Cl. ...................... 424/460; 525/54.2; 525/54.3; 525/535; 525/539; 525/540; 428/402.21; 428/402.24; 424/184.1; 424/193.1; 424/457; 424/461; 424/489; 424/493; 424/497; 424/499; 424/963; 264/4.1; 264/4.3; 264/4.4; 264/4.7; 514/951; 514/963; 514/2; 514/54
(58) Field of Search ............................... 525/54.2, 54.3, 525/535, 539, 540; 428/402.21, 402.24; 424/457, 460, 489, 461, 493, 497, 499, 184.1, 193.1, 963; 264/4.1, 4.3, 4.4, 4.7; 514/951, 963, 2, 54

(56) References Cited

U.S. PATENT DOCUMENTS

| 4,663,286 A | 5/1987 | Tsang et al. |
| 4,744,933 A | 5/1988 | Rha et al. |
| 4,749,620 A | 6/1988 | Rha et al. |
| 5,529,777 A | 6/1996 | Andrianov et al. |
| 5,585,183 A | 12/1996 | Chu |
| 5,645,827 A | 7/1997 | Marlin et al. |
| 5,654,004 A | 8/1997 | Okayama et al. |
| 5,700,459 A | 12/1997 | Krone et al. |

FOREIGN PATENT DOCUMENTS

WO    WO 99/18934 A    4/1999

OTHER PUBLICATIONS

Aoki H., Tottori, T., Sakuari F., Fuji K., Miyajima K., "Effects of Positive Charge Density on the Liposomal Surface on Disposition Kinetics of Liposomes in Rats" *Int. J. Pharm.*, 1997, vol. 156 (Oct. 24), pp. 163–174.

Burgess D. J., "Practical Analysis of Complex Coacervate Systems" *J. Collid Interf. Sci.*, 1990, Vol 140, No. 1. pp. 227–238.

Cabassi F., et al., "Infrared Absorption and Raman Scattering of Sulfite Groups of Hepasin and Related Glycosaminoglycans in Aqueous Solution", *Carbohydrate Research*, 1979, vol. 63, pp. 1–11.

Carpenter J.F., Izutsu K. I., Randolph T.W., "Freezing and Drying Induced Perturbation of Protein Structure and Mechanisms of Protein Protection by Stabilizing Additives" In *Freeze–Drying/Lyophilization of Pharmaceutical and Biological Products*, Rey, L. May J.C., Eds.; Marcel Dekker: New York, 1999.

Colthup N.B., Daly L.H., Wiberley S.E., Eds. "Introduction of Infrared and Raman Spectroscopy," $2^{nd}$ ed. New York: Academic Press, 1975, pp. 321–334.

Florence A.T., "The Oral Absorption of Micro–and Nanoparticulates: Neither Exceptional Nor Unusual", *Pharm. Res.* 1997, vol. 14, No. 3, pp. 259–266.

Gautier J.C., Grangier J.L., Barbier A., DuPont, P., Dussossoy D., Pastor G., Couvreu P., "Biodegradable Nanoparticles for Subcutaneous Administration of Growth Hormone Releasing Factor (hGRF)" *J. Control. Release*, 1992, vol. 20, pp. 67–78.

Grant A.C., Linhardt R. J., Fitzgerald G.L., Park J.J., Langer R., "Metachromatic Activity of Heparin and Heparin Fragments" *Anal. Biochem*, 1984, vol. 137, pp. 25–32.

Guerrero D. Q., Allemann E., Fessi H., Doelker E., "Preparation Techniques and Mechanisms of Formation of Biodegradable Nanparticles from Performed Polymers" *Drug Dev. Ind. Pharm.* 1998, vol. 24, No. 12, pp. 1113–1128.

Hoffman, F., Cinatl J.J., Kabickova H., Cinatl J., Kreuter J., Stieneker F., "Preparation, Characterization and Cytotoxicity of Methylmethacrylate Copolymer Nanoparticles with a Permanent Positive Surface Charge", *Int. J. Pharm.*, 1997, vol. 157, pp. 189–198.

Hosotsubo H., Hosotsubo K., "Improved High–Performance Liquid Chromatographic Determination of Amphotericin B In Human Serum and Plasma" *J. Pharm. Biomed. Anal.*, 1989, vol. 7, No. 8, pp. 975–979.

Koppel D.E., "Analysis of Macromolecular Polydisperisty in Intensity Correlation Spectroscopy; The Method of Cumulants" *J. Chemical Physics*, 1972, vol. 57, No. 11, pp. 4814–4820.

(List continued on next page.)

*Primary Examiner*—Samuel A. Acquah
(74) *Attorney, Agent, or Firm*—Kilpatrick Stockton LLP

(57) ABSTRACT

Compositions for sustained delivery of a biomolecule including an anionic polymer and a cationic polymer which ironically interact with each other and, optionally, with the biomolecule. Methods for making the compositions, including the step of combining the negatively charged polymer with the positively charged polymer to form an ionic complex are also provided. The biomolecule may be complexed with one of the polymers before it is complexed with the oppositely charged polymer. The complex is exposed to conditions that cause the formation of precipitated microcarriers, such as a change in pH or the addition of a complexing molecule. The compositions are preferably formulated into microcarriers.

15 Claims, No Drawings

OTHER PUBLICATIONS

Kreuter J., Nanoparticles, In Encyclopedia of Pharmaceutical Technology, vol. 10; Swarbrick J., Boylan J.C., Eds. Marcel Dekker Inc.: New York, 1988, p. 165–190.

Labhasetwar V., Song C., Humphrey W., Shebuski R., Levy R.J., "Arterial Uptake of Biodegradable Nanoparticels: Effect of Surface Modifications" *J. Pharm. Sci.*, 1998, vol. 87, No. 10, pp. 1129–1234.

Leo E., Vandelli M. A., Cameroni R., Forni F., "Doxorubicin–loaded Gelatin Nanoparticles Stabilized by Glutaraldehyde: Involvement of the Drug in the Cross Linking Process" *Int. J. Pharm.*, 1997, 155, pp. 75–82.

Li J.K., Wang N., Wu X. S., "A Novel Biodegradable System Based on Gelatin Nanoparticles and Poly(lactic–coglycolic acid) Microspheres for Protein and Peptide Drug Delivery" *J. Pharm. Sci.*, 1997, vol. 86, No. 8, pp. 891–895.

Madan P.L., "Microencapsulation I. Phase Separation or Coacervation" *Drug Dev. Ind. Pharm.*, 1978, vol. 4, No. 1, pp. 98–116.

Mirshahi T., Irache J.M., Gueguen J., Orecchioni A.M., "Development of Drug Delivery Systems From Vegetal Proteins: Legumin Nanoparticles" *Drug Dev. Ind. Pharm.*, 1996 vol. 22, No. 8, pp. 841–846.

Moore S., "Amino Acid Analysis: Aqueous Dimethyl Sulfoxide as Solvent for the Ninhydrin Reaction" *J. Biol. Chem.*, 1968, vol. 243, pp. 6281–6283.

Muller R. H., "Colloidal Cariers for Controlled Drug Delivery and Targeting" Boston: CRC Press; 1991, p. 3–18.

Muller R. H., et al., "Nanosurpensions," In Emulsions and Nanosuspression for the Formulation of Poorly Soluble Drugs, Muller, R. H., Benita S., Bohn B.H.L., Eds. Medpharm Scientific Publishers: Suttgart, Germany, 1998, p. 164.

Pikal M. J., "Freeze–Drying of Proteins. II FOrmulations Selection" *Biopharmaceutics*, Oct. 1990, vol. 3, pp. 26–29.

Pikal M.J., "Freeze–Drying of Proteins. I. Process Design" *Biopharmaceutics*, Sep. 1990, vol. 3, pp. 18–27.

Rey L. R., "Basic Aspects and Future Trends in the Freeze–Drying of Pharmaceuticals" *Developments in Biological Standardization*, vol. 74, May J.C., Brown F., Eds.; Karger: New York, 1990, pp. 3–8.

Shukla, A.J., Polymethacrylates pp. 362–366.

Suh J., Paik H–J., Hwang B.K., "Ionization of Poly (ethyleneimine) and Poly(allylamine) at various pH's" *Bioorg. Chem.* 1994, vol. 22, pp. 318–327.

Truong L. V., August J. T., Leong K. W., "Controlled Gene Delivery by DNA–Gelatin Nanospheres" *Human Gene Therapy*, 1998, vol. 9, No. 12, pp. 1709–1717.

English Abstract for German Patent Appl. Publication No. 00454044/EP B1. Patent Application No. 91106,495, Volker Krone, et al., "Pharmacological Product Containing Polyelectrolyte Complexes in Microparticulate Form and at Least One Substance".

English Abstract for German Patent Appl. Publication No. 00454044/EP A2. Patent Applicaion No. 91106,495, Volker Krone, et al., "Pharmacological Product Containing Polyelectrolyte Complexes in Microparticulate Form and at Least One Substance".

English Abstract for German Patent App. Publication No. 00431327/EP A1. Gunther Jung et al., "Synthetic Vaccine for the Specific Induction of Cytotoxic T–Lymphocytes".

English Abstract for JP 48055184A (XP002163981). "Encapsulation of Oleophilic Materials in Anionic and Cationic Hydrophilic Polymers Reaction Prod".

Peptoids Eyed for Gene Therapy Applications C&EN Science/Technology, May 4, 1998.

Microsphere Technology and Applications, pp. 1–18.

ns and methods for making microparticles, and more
IONICALLY FORMULATED BIOMOLECULE MICROCARRIERS Priority is claimed to PCT application No. PCT/US00/17223, filed Jun. 23, 2000, which claims the benefit of U.S. Provisional Application No. 60/140,623, filed Jun. 23, 1999; each of which is incorporated herein by reference.

FIELD OF THE INVENTION

The present invention relates to microparticle compositions and methods for making microparticles, and more particularly relates to ionically formed microcarriers for sustained release of biomolecules.

BACKGROUND OF THE INVENTION

Drug delivery systems have evolved greatly in the past ten years. Innovations in drug delivery systems have been driven by medical, technological, and economic factors. One focus has been the development of noninvasive drug delivery systems, which offer an improved quality of life for patients, and can provide improved bioavailability of drugs. Several new areas of development are the use of transdermal technologies and oral administration, both of which avoid the need for injections. Oral administration faces a problem with delivery of biomolecules, such as peptides, which can be rapidly broken down in the gastric cavity.

Another new area of development is delivery via the pulmonary system. Advantages of pulmonary delivery include lowered invasiveness compared to injection, high absorption of undegraded biomolecules, and the ability to target drugs to sites of respiratory disease.

A main focus of research on drug delivery has been providing for controlled release of drugs and continuous maintenance of an acceptable concentration of drugs. A recent success in this area has been an extended-release formulation of nifedipine commercially available as the Procardia XL® nifedipine formulation (Pfizer Inc., New York, N.Y.). The coupling of a biomolecule with a biodegradable polymer can provide controlled release by diffusion out of or degradation of the polymer and can also protect vulnerable drug formulations, such as peptides, from degradation.

Biodegradable polymers can be used for formulation of biomolecules for oral delivery, for implantable delivery systems, for pulmonary delivery, as well as for intravenous injection. Preferred polymers are those that are biodegradable and biocompatible, and that exhibit the desired release characteristics, generally a sustained rate of release without final "dumping" of biomolecule upon final hydrolysis of polymer.

Biodegradable polymers are often used in the form of microcarriers to deliver biomolecules. Advantages of the use of microcarriers include the ability to use appropriately sized carriers to target delivery. For example, microcarriers at least 15 microns in size can be used for regional or depot delivery, whereas delivery via inhalation requires particles in the one to five micron size. Other advantages include the ability to provide protection to delicate biomolecules prior to and during administration and ease of manufacture.

SUMMARY OF THE INVENTION

Compositions for sustained delivery of biomolecules are described herein. The compositions include an anionic polymer (polyanion) and a cationic polymer (polycation) which ionically interact with each other and, optionally, with the biomolecule to form a polymer matrix or complex. Also provided are methods for making the compositions, including the step of combining the negatively charged polymer with the positively charged polymer to form anionic complex. The biomolecule may be complexed with either one of the polymers, depending on the characteristics of the biomolecule, such as the charge of the biomolecule. Then the complex is reacted with the oppositely charged polymer. The complex is exposed to conditions, such as a change in pH or the addition of a complexing molecule, that cause the formation of precipitated microparticles, also referred to herein as microcarriers. The compositions are preferably formulated into microcarriers. The preferred polyanions and polycations are water soluble polymers, available commercially at high purity, that are already known and on the GRAS (generally regarded as safe) list. Alternatively, the polymers are high molecular positively or negatively charged polymers synthesized using polymer chemistry synthesis methods known to those skilled in the art.

In a preferred embodiment, the cationic polymer is polyethyleneimine (PEI), polychitosan, or a cationic polymethacrylate, and the anionic polymer is dextran sulfate, heparin, alginic acid or an anionic polymers are available in a range of molecular weights, typically in the range of 20,000 to 500,000 kD.

Most preferably, insulin, a positively charged protein, is first complexed with dextran sulfate. The cationic polymer, PEI or DEAE dextran, is than added and complexed with the insulin/dextran sulfate complex. Formation of microcarriers is initiated by addition of zinc sulfate.

In another preferred embodiment, the cationic polymer is polyethyleneimine (PEI) and the anionic polymer is dextran sulfate or alginic acid. A negatively charged biomolecule, such as a nucleic acid, is first complexed with the PEI. The biomolecule/PEI complex is than complex with dextran sulfate. Formation of microcarriers is initiated by the addition of zinc sulfate.

Accordingly, it is an object of the invention to provide compositions for the delivery of biomolecules comprising microcarriers that release biomolecules at a sustained, constant rate of release.

It is another object of the present invention to provide compositions for delivery of biomolecules comprising microcarriers that provide stability to biomolecules during formulation and after administration.

It is another object of the present invention to provide microparticle compositions for the delivery of drugs in which the toxic effects of the drugs are minimized by being incorporated in a sustained-release microparticle formulation.

It is another object of the present invention to provide microparticle vaccines for the delivery of antigens in which an immunogenic effect is achieved in the absence of an adjuvant.

It is another object of the present invention to provide microparticle vaccines in which the polymers of the microparticles have an adjuvant effect.

These and other objects of the present invention will become apparent after reading the following detailed description of the disclosed embodiments and the appended claims.

DETAILED DESCRIPTION OF THE INVENTION

A microparticle composition, also referred to herein as a microcarrier composition, and method for forming microparticles, or microcarriers, for the delivery of biomolecules, such as proteins, peptides, polynucleic acids, and drugs, as well as larger biomolecules such as bacteria and viruses are provided. Preferably, the biomolecules in the microcarrier composition are in biologically active form or are immunogenic and are then released gradually in situ from the microcarrier when administered to a human or animal subject. The microcarriers are formulated using a mixture of water-soluble, positively and negatively charged polymers that interact with each other via ionic bonds. The biomolecule is optionally complexed with either the anionic polymer or the cationic polymer, depending upon the net charge of the biomolecule. The complexed biomolecule and polymer is then complexed with the oppositely charged polymer to form a combined complex in solution. Microcarriers are then formed by initiating coacervation, such as by changing the pH of the solution or adding a precipitating agent, such as zinc sulfate or certain amino acids.

MICROPARTICLE COMPOSITIONS

The microparticle compositions described herein contain a biomolecule, a cationic polymer and an anionic polymer. In a preferred embodiment, the biomolecule is complexed to either the cationic or anionic polymer. The complexed biomolecule/polymer is then complexed to the other polymer and microcarriers are formed. Preferably, the polymers are aqueous biodegradable polymers. Aqueous solutions are preferred over organic solutions because degradation of the biomolecule is avoided as is the use of chemical that may be toxic and therefore removed and recovered during the manufacturing process.

The preferred composition is a microparticle, microcarrier, or micromatrix, in which the biomolecule is homogeneously distributed throughout a polymer meshwork, thereby resulting in more uniform biomolecule release during in vivo degradation.

Biomolecules

A wide variety of biomolecules can be delivered using the compositions. The term biomolecule as used herein refers to bioactive, diagnostic, and prophylactic molecules. Biomolecules that can be used in the present invention include, but are not limited to, synthetic, recombinant or isolated peptides and proteins such as antibodies and antigens, receptor ligands, enzymes, and adhesion peptides; nucleotides and polynucleic acids such as DNA and antisense nucleic acid molecule; activated sugars and polysaccharides; bacteria; viruses; and chemical drugs such as antibiotics, antiinflammatories, and antifungal agents. Examples of proteins and peptides include insulin, luteinizing hormone release hormone (LHRH), somatostatin, calcitonin, vasopressin, epidermal growth factor (EGF), tissue plasminogen activator (TPA), human growth hormone, interleukins such as IL-2, interferon, erythropoietin (EPO) and others. Examples of other drugs that can be used in the compositions are amphotericin B (AMP-B), doxorubicin, and morphine sulfate.

Exemplary diagnostic agents include diagnostic enzymes and radiolabelled and fluorescent compounds.

Cationic Polymers

The cationic polymer of the microcarrier is a water soluble, positively charged polymer. Examples of cationic polymers that can be used in the invention include, but are not limited to, DEAE dextran (diethyleneaminoethyl dextran), polyethyleneimine (PEI), chitin, chitosan (D-acetylated chitin), and polyamino acids with a positive charge, such as polylysine. Peptoids, which are N-substituted polyglycines, achiral peptide variants in which side chains are sited on the amide nitrogen atom of each glycine monomer, have been shown to complex with plasmid DNA and can be used as the cationic polymer.

Anionic Polymers

The anionic polymer of the microcarrier is a water soluble, negatively charged polymer. Examples of anionic polymers that can be used in the present invention include, but are not limited to, dextran sulfate, heparin, and polyamino acids having a negative charge. Gel forming anionic polymers can be used, such as alginate and carageenan.

Precipitation Agent

The complexed polymers can be precipitated to form the microcarriers by changing the pH of the solution. Microcarriers can also be formed by adding a complex forming agent to the solution. For example, zinc sulfate and other multivalents salts will cause complexing of certain charged polymers. The size of the microcarriers is proportional to the concentration of the polymers and the amount of acid used to lower the pH or the amount of zinc sulfate used to cause formation of the microcarriers.

Microcarriers

The term microcarriers as used herein refers to carriers having a diameter measured in micrometers as well as nanometers. Preferably, the microparticles described herein have a diameter between 5 nm and 1000 microns. A more preferred range of the diameter of the microcarriers is between 50 nm and 30 microns. The term microcarriers refers to solid microparticles as well as hollow microspheres and microgranules. The microcarriers can be spherical or have other shapes. The size of the microcarriers can be varied to suit the appropriate use, such as, for example intravenous, oral or pulmonary delivery. Microcarriers having a diameter of at least fifteen microns are useful for regional or depot delivery, whereas delivery via inhalation requires smaller particles in the one to five micron size. Intravenous administration generally requires nanoparticles, in the 20 to 300 nm range, preferably 50 to 150 nm.

Other Excipients

Excipients such as polyalcohols can be used to stabilize the biomolecule. Examples are mannitol and trehalose. Surfactants can also be used to add stability. Examples include Tween®, cationic detergents such as cetyltrimethylammonium chloride, and anionic phospholipids such as diolylphosphatidylglycerol.

METHODS OF MAKING MICROPARTICLE COMPOSITIONS

The microparticle compositions described above are generally prepared by incorporating the biomolecule within a complex formed by the cationic polymer and the anionic polymer. Preferably, the biomolecule is itself ionically bound to one of the polymers. Alternatively, the biomolecule may be merely physically surrounded by the polymeric complex.

Biomolecules that are positively charged, such as some peptides, can be first reacted with the anionic polymer in solution. The cationic polymer is then added and mixed with the biomolecule/anionic polymer complex. Other biomolecules, such as DNA are reacted first with the cationic polymer and the anionic polymer is then added to the reaction mixture. A catalyst may also be added to enhance the reaction. Preferably, the catalyst is combined with the second polymer that is added to the reaction mixture.

Microcarrier formation is initiated by causing precipitation of the complex. An acid, preferably a dilute acid such as acetic acid or hydrochloric acid, can be added to lower the pH to the point where the reaction becomes cloudy. In most cases, this will be a pH of approximately 5 to 8. Alternatively, salts, such as zinc sulfate, can be added to the solution until the solution becomes cloudy. Certain amino acids that bring the pH into the range of microparticle formation may alternatively be used.

Biomolecules that are negatively charged such as plasmid DNA, can be first reacted with the positively charged polymer, such as polyethyleneimine or polylysine. The anionic polymer is then added to the complex of biomolecule and cationic polymer, whereupon it complexes with the cationic polymer. Again, as the complex is precipitated by lowering the pH is lowered or adding zinc sulfate as described above, microcarriers are formed.

In another embodiment, the anionic and cationic polymers and the biomolecule can be combined to form a polymeric complex entrapping the biomolecule. The complex is then precipitated into microcarriers using a precipitation agent, such as zinc sulfate.

Unlike many conventional particle formation methods, the microparticles described herein are formed in the absence of heat. Therefore, preferably both the polymer complex formation step and the precipitation step are conducted at a temperature between 4° C. and room temperature. The absence of adverse reaction conditions, such as elevated temperatures, enhances the bioactivity or immunogenicity of the biomolecule incorporated in the microparticle.

The polymers are preferably provided in a concentration of about 0.1 to 20 weight percent, most preferably about 1 weight percent. The polymers are mixed in a weight ratio of 1:9 to 9:1, preferably about 1:4 to 4:1, most preferably about 1:1. The polymers are mixed in a charge ratio of 1:3 to 3:1, most preferably about 1:1. The ratio to be used is a function of the particle size and drug loading capacity desired.

The amount of biomolecule present greatly depends upon the dosage desired for the biomolecule and the degree of interaction between the biomolecule and one or more of the polymers. A highly charged biomolecule can be retained by the polymeric complex in much higher concentration than a relatively uncharged biomolecule. Preferably, biomolecules are incorporated into the microparticle with an efficiency of 80 to 90%. One skilled in the art can determine appropriate amounts of biomolecule.

The size of the microcarriers can be controlled by the concentration of the polymers, the charge ratio of the polymers, the molecular weight of the polymers, and the pH of the reaction. The ability to control microparticle size is especially important for administration of the biomolecule to a human or animal subject. As described above, particular diameter ranges are required for certain routes of administration, such as the need for nanoparticles when intravenous administration is employed.

The microparticles are separated from the non-incorporated components of the incubation mixture by conventional separation methods well known to those skilled in the art such as centrifugation, filtration and sedimentation. Preferably, the reaction mixture is centrifuged so that the microparticles sediment to the bottom of the centrifuge tube and the non-incorporated components remain in the supernatant, which is then removed by decanting. Alternatively, a suspension containing formed microparticles is filtered so that the microparticles are retained on the filter and the non-incorporated components pass through the filter.

Further purification of the microparticles is achieved by washing in an appropriate volume of a washing solution. The preferred washing solution is a buffer, most preferably a nonionic aqueous solution or a nonionic aqueous solution containing water soluble polymers. Repeated washings can be utilized as necessary and the microparticles separated from the wash solution as described above.

The final microparticle composition may be lyophilized, stored as a wet cake, or formulated in solution for final use.

Microparticle Post-production Treatment

The microparticles are optionally treated after production to enhance or impart particular characteristics to the microparticles, such as stability, detectability, and prolonged release. For example, vanillin can be added to stabilize the biomolecule and help prolong its release by rendering the biomolecules less soluble the matrix.

The microparticles are optionally labelled with a detectable label using various types of labels and methods of labelling molecules well known to those skilled in the art. For example, the label can be a metal, a radiolabel, or a Mass or Nuclear Magnetic Resonance (NMR) label. Dyes, chemiluminescent agents, bioluminescent agents and fluorogens can also be used to label the microparticles. The microparticles can also be labelled with a chromogen, or enzyme to produce a chromogenic or fluorogenic reaction upon addition of substrate. Alternatively, the microparticles can be biotinylated and utilized in a biotin-avidin reaction, which may also be coupled to a label such as an enzyme or fluorogen. A label can also be made by incorporating any modified base, amino acid, or precursor containing any label, incorporation of a modified base of amino acid containing a chemical group recognizable by specific antibodies, or by detecting any bound antibody complex by various means including immunofluorescence or immunoenzymatic reactions. Such labels can be detected using enzyme-linked immunoassays (ELISA) or by detecting a color change with the aid of a spectrophotometer.

Molecules may be attached to the outer surface of the microparticles by methods known to those skilled in the art to "coat" the microparticles. These molecules are attached for purposes such as to enhance stability and facilitate targeting. For example, biomolecules such as phospholipids may be attached to the surface of the microparticle to prevent endocytosis by endosomes; receptors, antibodies or hormones may be attached to the surface to promote or facilitate targeting of the microparticle to the desired organ, tissue or cells of the body; and polysaccharides, such as glucans, may be attached to the outer surface of the microparticle to enhance or to avoid uptake by macrophages. The microparticles may also be coated with one or more stabilizing substances, which may be particularly useful for long term depoting with parenteral administration or for oral delivery by allowing passage of the microparticles through the stomach or gut without dissolution. For example, microparticles intended for oral delivery may be stabilized with a coating of a substance such as mucin. Additionally, the particles can be non-covalently coated with compounds such as fatty acids or lipids. The coating may be applied to the microparticles by immersion in the solubilized coating substance, spraying the microparticles with the substance or other methods well known to those skilled in the art.

METHODS OF USING MICROPARTICLE COMPOSITIONS

The compositions are useful for producing microcarriers for use in the delivery of the complexed biomolecule. The biomolecule is useful for achieving a therapeutic, diagnostic or prophylactic effect. The microcarriers may be used for oral or pulmonary delivery of a biomolecule or via intravenous injection. The microcarriers are also useful in methods involving transdermal drug delivery as well as subcutaneous and intramuscular delivery.

A particular use of the microcarriers is in vaccine formulation. Microparticles containing antigens capable of provoking an immune response as the biomolecules are particularly suitable for use as vaccines. It has been unexpectedly discovered that the polymers of the microparticles described herein, particularly polyethyleneimine and dextran sulfate, have adjuvant effects. Therefore, the microparticles produce an immunogenic effect when administered to a human or animal subject in the absence of a conventional adjuvant, such as aluminum hydroxide (alum).

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Production of Insulin Microcarriers Using Polyethyleneimine

A one percent (1%) aqueous solution of polyethyleneimine was made and stored at 4° C. A one percent (1%) aqueous solution of dextran sulfate was made and stored at 4° C. The pH of the polyethyleneimine solution was adjusted to 9.3 to 9.7. The pH of the dextran sulfate solution was adjusted to 6.8 to 7.2. 0.5 ml of 1 M zinc sulfate was added to 50 ml of the polyethyleneimine solution and mixed with about 5 ml of glacial acetic acid to adjust the pH to 5.5 to 5.8.

Ten mg of bovine insulin was dispersed in 1 ml $H_2O$. Twenty µl of 1 N HCl was added. This solution was added to 5 ml of the dextran sulfate solution and the pH was adjusted to 6.8 to 7.1. The solution was mixed for 30 minutes at room temperature, whereupon 0.5 to 2.0 ml of polyethyleneimine solution was added according to the scheme in Table 1 below.

TABLE 1

| Tube | Reaction Mixture | PEI Solution added |
|------|------------------|--------------------|
| A | 1 ml | 0.5 ml |
| B | 1 ml | 1.0 ml |
| C | 1 ml | 1.5 ml |
| D | 1 ml | 2.0 ml |

Each tube was mixed for 30 minutes at room temperature. The particulate matter was centrifuged and washed three times with water. Microparticles were formed having a diameter of about three to 15 microns.

EXAMPLE 2

Production of Insulin Microcarriers Using DEAE Dextran

The protocol set forth above in Example 1 was generally followed using a solution of 1% DEAE dextran in water adjusted to a pH of 9.3 to 9.7, instead of the solution of PEI, according to the following scheme, set forth in Table 2.

TABLE 2

| Tube | Reaction Mixture | DEAE Dextran Solution added |
|------|------------------|------------------------------|
| A | 1 ml | 25 µl |
| B | 1 ml | 50 µl |
| C | 1 ml | 75 µl |
| D | 1 ml | 100 µl |

Microparticles were formed having a diameter of about three to 15 microns.

EXAMPLE 3

Production of AMP-B Microcarriers Using PEI

Ten micrograms of amphotericin B (AMP-B) were mixed with one ml of water and ten microliters of 1 N HCl. One ml of DMSO was added to facilitate solution. Five milliliters of dextran sulfate solution prepared as in Example 1 were added and mixed for 30 minutes at room temperature. The reaction mixture was wrapped in foil in order to avoid light exposure. As in Example 1, four samples were prepared using 0.5, 1.0, 1.5, and 2.0 ml of the PEI solution. Microparticles were formed having a diameter of about three to 15 microns.

EXAMPLE 4

Production of a AMP-B Microcarriers Using DEAE Dextran

The procedure of Example 2 was followed but using DEAE dextran solution instead of PEI solution. The AMP-B solution of Example 3 was used. Microparticles were formed having a diameter of about three to 15 microns.

EXAMPLE 5

Production of Plasmid DNA Microcarriers Using Dextran Sulfate

A 1% solution of dextran sulfate in water, pH 6.8 to 7.2, a 1% solution of polyethyleneimine, pH 9.4 to 9.6, and 1 M solution of zinc sulfate in 1 N glacial acetic acid were used. Ten ml of 50/50 dextran sulfate and polyethyleneimine were prepared and the absorbency at 260 nm recorded. Plasmid DNA to a final concentration of 50 micrograms per milliliter was added and the absorbency at 260 nm recorded. Two hundred microliters of the zinc sulfate solution was added to 2 ml of the plasmid/polymer mixture and the resulting solution centrifuged for three to five minutes at 2500 to 3000 rpm. The supernatants were removed and the absorbencies of the supernatants measured at 260 nm. The absorbance of the dextran sulfate/PEI solution was 0.287. The absorbance of the DNA plasmid/polymer solution was 1.285. The absorbency of the supernatant was 0.138, indicating that the majority of the plasmid DNA was contained in the pellet. The pellet contained large particle.

EXAMPLE 6

Production of Heparin Microcarriers Using PEI

Heparin microcarriers were prepared as descried in Example 1, above. Freshly collected human blood was incubated with the heparin microcarriers. The bound heparin demonstrated similar anticoagulant activity as normal untreated heparin. Heparin is normally lyophilized for storage, as it otherwise has a short shelf-life. The microcarriers used in this example were stored for ten days at 4° C. prior to use and still showed very good activity.

EXAMPLE 7

Production of Insulin Microcarriers Using PEI

Insulin microcarriers (microparticles) were prepared as follows. A 10 mg/ml aqueous solution of polyethyleneimine was made and stored at 4° C. a 10 mg/ml aqueous solution of dextran sulfate was made and stored at 4° C. The pH of the polyethyleneimine solution was adjusted to pH 10 using 1N HCl. A 5 mg/ml aqueous solution of insulin in 0.01 N HCl was adjusted to pH 7 with 0.5 N NaOH.

The reaction mixture contained 0.2 ml of the insulin solution, 0.1 to 0.3 ml of the dextran sulfate solution, 0.2 to 0.4 ml of the polyethyleneimine solution, 0.02 to 0.05 ml of the zinc sulfate solution and water to 1.0 ml. The reaction mixture was prepared by mixing the water, dextran sulfate, polyethyleneimine and insulin for five minutes, then adding the zinc sulfate and stirring for 15 minutes.

A mass ratio of dextran sulfate:polyethyleneimine in the range of 0.3 to 0.7 produced nanoparticles. A mass ratio of dextran sulfate:polyethyleneimine in the range of more than 0.7 produced microparticles.

EXAMPLE 8

Production of DNA Microcarriers Using PEI

DNA microparticles were prepared as follows. A 10 mg/ml aqueous solution of polyethyleneimine was made and stored at 4° C. A 10 mg/ml aqueous solution of dextran sulfate was made and stored at 4° C. The pH of the polyethyleneimine solution was adjusted to 10 using 1 N HCl. A 0.5 mg/ml aqueous solution of DNA in water was prepared.

The reaction mixture contained 0.1 to 0.3 ml of the DNA solution, 0.1 to 0.3 ml of the dextran sulfate solution, 0.2 to 0.5 ml of the polyethyleneimine solution, 0.016 to 0.025 ml of the zinc sulfate solution and water to 1.0 ml. The reaction mixture was prepared by mixing the water, dextran sulfate, polyethyleneimine and DNA for five minutes, then adding the zinc sulfate and stirring for 5 minutes.

Nanoparticles were produced. Microparticles were produced when higher or lower concentrations of zinc sulfate were used or higher concentrations of DNA were included.

The above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference.

What is claimed is:

1. A microparticle composition for delivery of a biomolecule comprising a biomolecule incorporated in a complex comprising a cationic polymer ionically complexed with an anionic polymer, wherein the cationic polymer is polyethyleneimine and the anionic polymer is dextran sulfate.

2. The microparticle composition of claim 1 wherein the biomolecule is ionically complexed with the cationic or anionic polymer.

3. The microparticle composition of claim 1 wherein the biomolecule is selected from the group consisting of proteins, peptides, polynucleic acids, polysaccharides, bacteria, viruses, and drugs.

4. The microparticle composition of claim 1 wherein the diameter of the microparticle is between 50 nm and 30 microns.

5. A method for producing microparticles comprising
   reacting a biomolecule, a cationic polymer, and an anionic polymer to form an ionically bonded complex of the polymers, wherein the biomolecule is incorporated in the polymer complex, the cation polymer is polyethyleneimine, and the anionic polymer is dextran sulfate, and
   precipitating the complex to form the microparticles.

6. The method of claim 5 wherein the biomolecule is bound to one of the polymers prior to reacting the polymers.

7. The method of claim 5 wherein the complex is precipitated by adding a salt or acid to the complex.

8. The method of claim 5 wherein the biomolecule is selected from the group consisting of proteins, peptides, polynucleic acids, polysaccharides, bacteria, viruses, and drugs.

9. The method of claim 5 wherein the complex is ionically bonded polymers is formed in the absence of heat.

10. The method of claim 5 wherein the complex of ionically bonded polymers is formed at a temperature between 4° C. and room temperature.

11. The method of claim 5 wherein the diameters of the microparticles are between 50 nm and 30 microns.

12. The method of claim 5 wherein the diameters of the microparticles are between 20 and 300 nm.

13. The method of claim 5 wherein the concentration of each polymer reacted is between 0.1 and 20 weight percent.

14. A method for delivering a biomolecule to a human or animal subject comprising administering to the subject a microparticle composition comprising a biomolecule incorporated in a complex comprising a cationic polymer ionically complexed with an anionic polymer, wherein the microparticle releases the biomolecule in vivo, and wherein the cationic polymer is polyethyleneimine and the anionic polymer is dextran sulfate.

15. The method of claim 14 wherein the biomolecule is an antigen and the microparticle causes an immunogenic effect in the absence of an adjuvant when administered to the subject.

* * * * *